United States Patent [19]
van den Honert et al.

[11] Patent Number: 5,000,194
[45] Date of Patent: Mar. 19, 1991

[54] ARRAY OF BIPOLAR ELECTRODES

[75] Inventors: Christopher van den Honert, Maplewood; David C. Michow, Richfield, both of Minn.

[73] Assignee: Cochlear Corporation, Englewood, Colo.

[21] Appl. No.: 236,516

[22] Filed: Aug. 25, 1988

[51] Int. Cl.$^5$ .............................................. A61N 1/05
[52] U.S. Cl. ................................ 128/784; 128/420.6; 623/10
[58] Field of Search ................ 623/10; 128/420.6, 784

[56] References Cited

U.S. PATENT DOCUMENTS

| | | | |
|---|---|---|---|
| 4,284,856 | 8/1981 | Hochmair et al. | |
| 4,750,499 | 6/1988 | Hoffer | 128/784 |
| 4,762,135 | 8/1988 | van der Puije et al. | 128/784 |
| 4,819,647 | 4/1989 | Byers et al. | 128/784 |
| 4,832,051 | 5/1989 | Jarvik et al. | 128/784 |

FOREIGN PATENT DOCUMENTS 1115352 12/1981 Canada .............................. 128/784

OTHER PUBLICATIONS

Rubinstein et al., Recessed and Surface-Mounted Electrodes for Auditory Prostheses: Effects on Histopathology, *Abstracts of the Tenth Midwinter Research Meeting, Association for Research in Otolaryngology* (Feb. 1–5, 1987).
Hochmair-Desoyer et al., Design and Fabrication of Multi-Wire Scala Tympani Electrodes, *Annals of the New York Academy of Sciences*, vol. 405, pp. 173–182.
Loeb et al., Design and Fabrication of an Experimental Cochlear Prosthesis, *Medical & Biological Engineering and Computing*, vol. 21, pp. 241–244 (May 1983).
Clark et al., A Cochlear Implant Round Window Electrode Array, *The Journal of Laryngology and Otology*, vol. 93, pp. 107–109 (Feb. 1979).
van den Honert, Single Fiber Mapping of Spatial Excitation Patterns in the Electrically Stimulated Auditory Nerve, *Hearing Research*, vol. 29, pp. 195–206 (1987).

Primary Examiner—Randall L. Green
Assistant Examiner—Stephanie L. Iantorno
Attorney, Agent, or Firm—Gottlieb, Rackman & Reisman

[57] ABSTRACT

The invention provides an array of electrodes suitable for use as an auditory prosthesis. The array comprises a carrier member formed from electrically insulating flexible material, having a surface and a core, the carrier member including at least a pair of electrodes molded therein, the electrodes comprising a length of contact material formed in a semi-circular shape, having a convex contact surface and a locking portion defining an internal space. The electrode is molded in the carriers so that the convex contact surface of the electrode is preferably flush with the carrier member surface. The locking portion of the electrode is molded into the core of the carrier member in the electrode connected to a lead wire which is molded in the core of the carrier member. The invention further provides a method for fabricating such an array of bipolar electrodes.

9 Claims, 2 Drawing Sheets ns and being planar# ARRAY OF BIPOLAR ELECTRODES

TECHNICAL FIELD

This invention relates to an array of radially oriented bipolar pairs of electrodes, particularly for use as an auditory prosthesis.

BACKGROUND OF THE INVENTION

Electrical stimulation of auditory nerve fibers in persons with total sensory deafness has been found to produce auditory sensations which can be perceived with sufficient familiarity, that with minimal training such sensations can be used for speech reception without additional cues. Electrical stimulation of the auditory nerve fibers in deaf patients is accomplished by a number of methods. Many methods of stimulating the auditory nerve fibers utilize an array of electrodes mounted in a flexible worm-like carrier which is inserted into the cochlea region of a patient's ear.

The human cochlea has a snail-like configuration; thus, two basic mechanical designs have existed for intracochlear arrays of electrodes. The first design has a shape which matches the coiled structure of the human cochlea. A prosthesis of this design is temporarily straightened before insertion and regains its coiled shape upon insertion in the cochlea. The second design is a straight prosthesis which is very flexible, but which has sufficient stiffness to be guided into the cochlea in the desired coiled shape. The straight flexible configuration is often preferred. See Hochmair-Desoyer et al., *Design and Fabrication of Multi-Wire Scala TYmpani Electrodes*, Vol. 405, Annals of the New York Academy of Sciences, pp. 173-182.

The straight flexible auditory prosthesis will typically have an array of electrodes of various shapes, and positioned in one of a number of various configurations along the length of the prosthesis. These various configurations include monopolar electrodes and bipolar pairs of electrodes, which pairs may be positioned either radially or longitudinally along the flexible prosthesis. See Loeb et al., Design and Fabrication of an Experimental Cochlear Prosthesis, *Medical & Biological Engineering and Computing*, May 1983, Vol. 21, pp. 241-254 ("Loeb"); Clark et al., A Cochlear Implant Round Window Electrode Array, *The Journal of Laryngology and Otology*, February 1979, Vol. 93, pp. 107-109.

An auditory prosthesis having a radial bipolar configuration appears to be the most favorable electrode geometry for the multiple electrode array. See, Van den Honert et al., Single Fiber Mapping of Spatial Excitation Patterns in the Electrically Stimulated Auditory Nerve, *Hearing Research*, 29 (1987) pp. 195-206.

In addition to having a radial bipolar configuration, it is desirable that the array of electrodes have a large surface area with individual electrodes having a surface area of greater than about 0.25 mm2. The flexible prosthesis should also be capable of being easily fabricated, the metal electrodes should displace small volumes of carrier material and lock the electrode into the carrier material so that the edges cannot pop out.

Previous constructions have included so-called flame balls which are made by melting the ends of platinum or platinum-iridium wires. Known practical flame ball constructions have longitudinal configurations as the internal volume of the flame balls does not permit radially placed electrodes. In the Loeb reference, electrodes are made by swedging a flame ball into a desired shape. However, these electrodes are subject to similar internal volume problems. Another known configuration is that of electrode rings, which are longitudinally spaced apart.

SUMMARY OF THE INVENTION

Therefore, there is a need for a flexible array of electrodes, for use, for example as an auditory prosthesis which has a large contact surface area, which has electrodes which displace small volumes of carrier material, which provides a configuration of electrode which locks the edges of the electrode into the carrier material, and which can be easily formed.

The invention provides an array of electrodes, suitable for use, for example, as an auditory prosthesis, the array comprising a carrier member formed from an electrically insulating flexible material, having a surface and a core, the carrier member including at least one pair of electrodes molded therein, the electrodes comprising a length of contact material formed in a semi-circular shape, having a convex contact surface and a locking portion defining an internal space, the electrode molded in the carrier so that the convex contact surface of the electrode is preferably flush with the carrier member surface, the locking portion of the electrode molded into the core of the carrier member and the electrode connected to a lead wire molded in the core of the carrier member. The carrier member is preferably elongate.

The invention further provides a method for fabricating an array of bipolar electrodes which comprises providing a length of contact material having a pair of edges, forming the length into a semi-circular shape so that the length of contact material includes a convex contact surface and a locking portion defining an internal space of semi-circular cross-section, and molding the length into a carrier member of an electrically insulating flexible material, the length of contact material oriented in the carrier so that the locking portion extends into the core of the carrier member to lock the electrode in place and so that the convex contact surface is preferably flush with the surface of the carrier.

DETAILED DESCRIPTION

Figure 1:
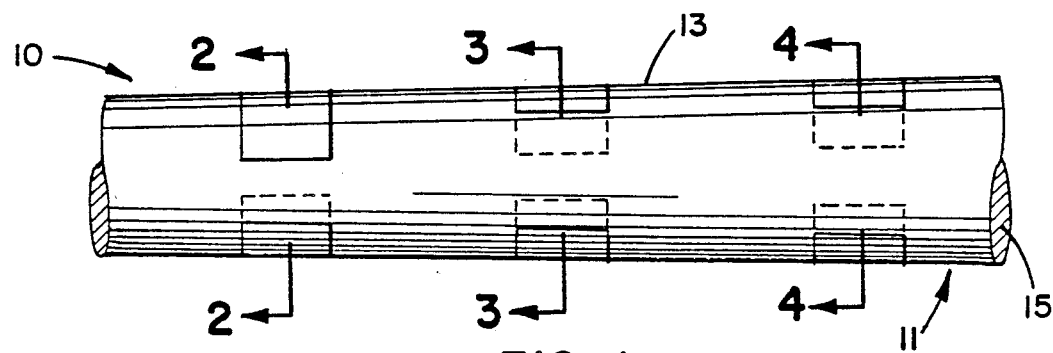
FIG. 1 is a partial perspective view of an electrode array of an embodiment of the present invention.

Referring to FIG. 1, an electrode array 10 of an embodiment of the present invention is shown. In practice, the preferred embodiment would contain, for example, 10 pairs of radially positioned electrodes. The electrode array 10 is an elongated body, having a radial cross-section which is preferably circular, and the body tapered longitudinally. The array includes a carrier member 11, having a surface 13 and a core 15.

Figure 2:
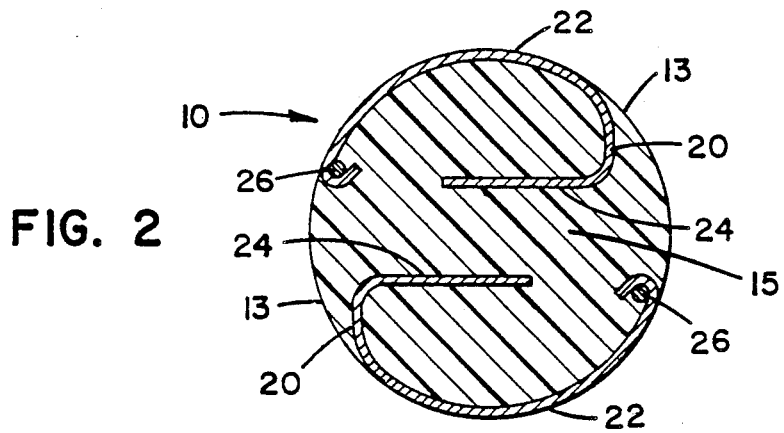
FIG. 2 is a cross-section along line 2—2 of FIG. 1.

Referring to FIG. 2, a cross-section of an array 10 of one embodiment of the present invention is shown. In the embodiment shown in FIG. 2, a pair of electrodes 20, each having a semi-circular shape and being planar in a longitudinal direction of the carrier member is shown. Each electrode has a convex contact surface 22 and a locking portion 24. The contact surface 22 is flush with the surface 13 of the carrier member 11 as is preferred. The locking portion 24 is secure in the core 15. Each electrode has a pair of lead wires 26 to electrically connect the electrodes 20.

Figure 3:
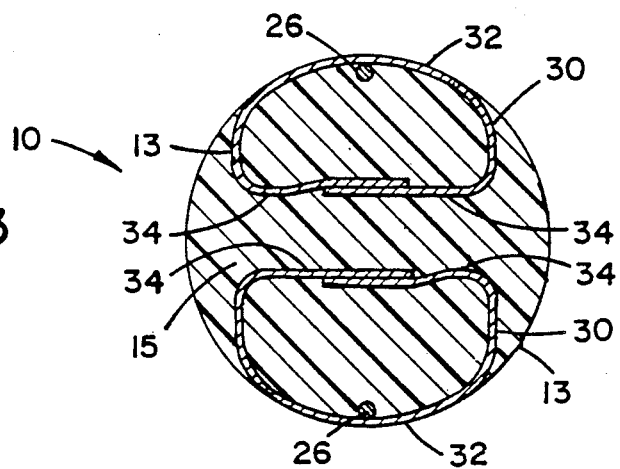
FIG. 3 is a cross-section along line 3—3 of FIG. 1.

Referring to FIG. 3, a cross-section of another embodiment in an array 10 of the present invention is shown. A pair of electrodes 30 having convex contact surfaces 32 and locking portions 34 are shown. The contact surface 32 is flush with the surface 13 of the carrier member 11. The locking portions 34 are locked in the core 15. Lead wires 26 are electrically coupled to the electrodes 30 in the underside of the convex contact surface portion 32.

Figure 4:
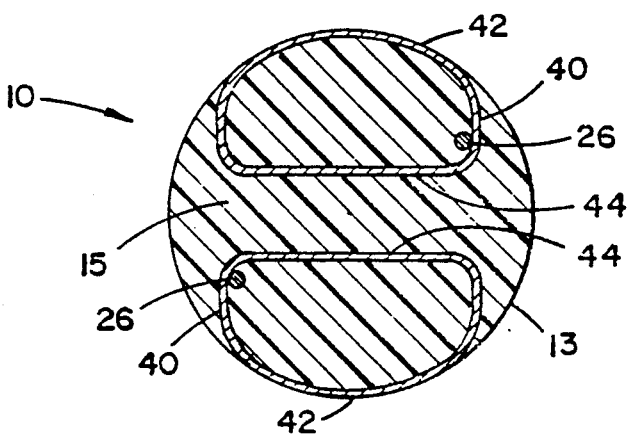
FIG. 4 is a cross-section along line 4—4 of FIG. 1.

Referring to FIG. 4, a cross-section of an array 10 of another embodiment of the present invention is shown, having a pair of electrodes 40 having convex contact surfaces 42 and locking portion 44. The contact surface 42 is flush with the surface 13 of the carrier member 11. The locking portion 44 is locked in the core 15. Lead wires 26 are electrically coupled by welding to the inside of the electrode 40. The electrodes depicted in FIG. 4 are continuous rings as opposed to folded strips of contact material as depicted in FIGS. 2 and 3.

Figure 5:
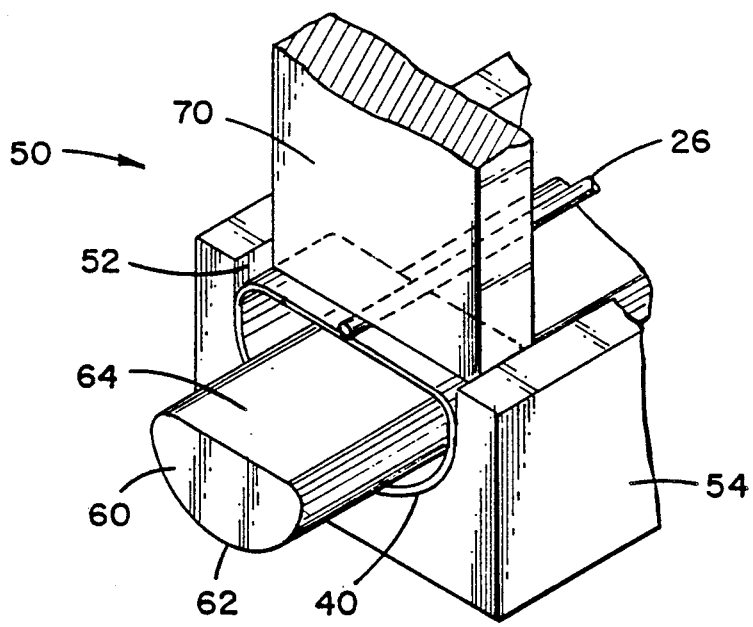
FIG. 5 is an isometric view of a contact material forming mold.

Referring to FIG. 5, an electrode forming mold 50 is shown. The mold includes a forming surface 52 and a mold body 54. The surface 52 has the same configuration as the desired shape of the electrode, typically of semi-circular cross-section. An electrode 40 is shown, formed from a ring of contact material. A spacer 60 is placed in the interior space of the electrode 40. The spacer 60 has a curved forming surface 62 and a locking means forming surface 64. A lead wire 26 is electrically coupled by welding to the electrode 40 in a desired position.

To form the electrode 40 into its desired shape, a ring of contact material having a void (not shown) is provided and the spacer 60 is placed through the void in the ring. A forming mandrel 70 is used to press the contact material and spacer 60 into the mold 50 to configure the contact material into the shape of the forming surface 52. The locking portion 44 is formed by the mandrel 70 pressing the material against the locking means forming surface 64.

Figure 6:
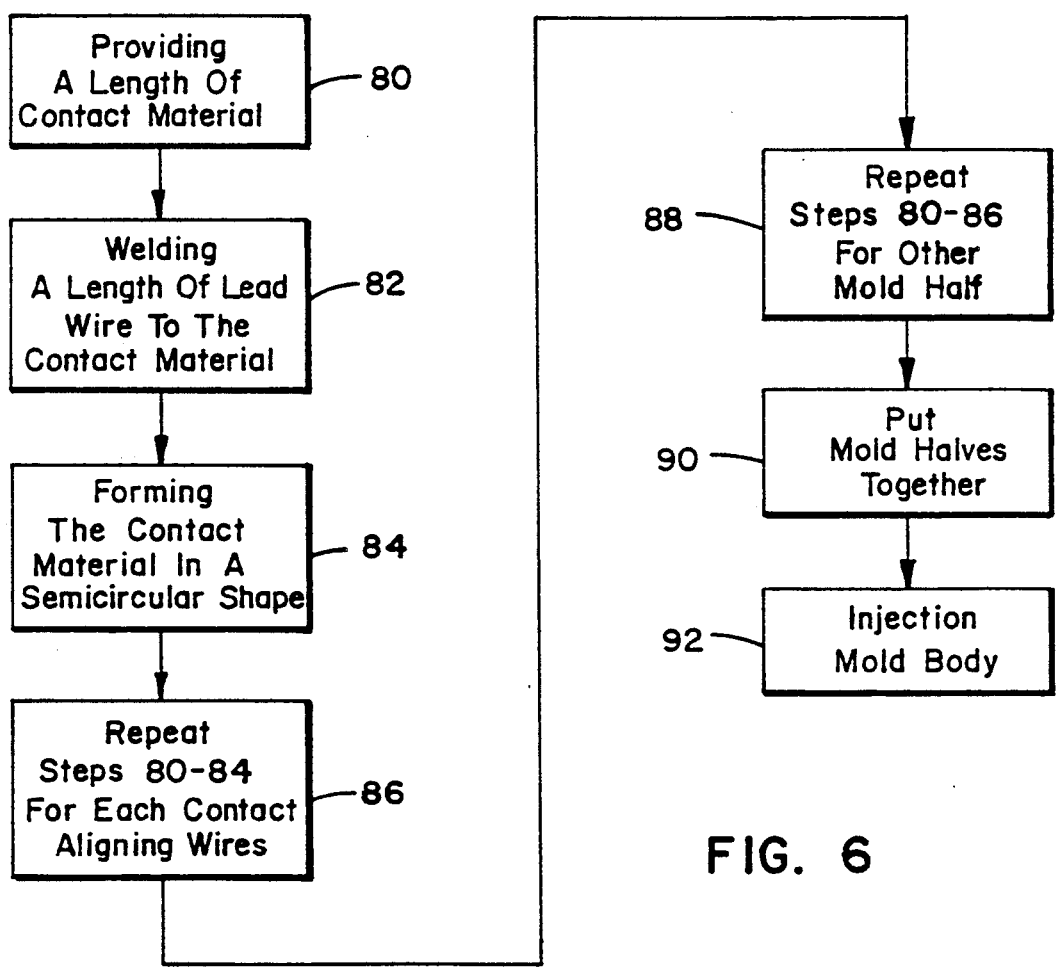
FIG. 6 is a flow chart of a preferred method of the present invention.

Referring to FIG. 6, a flow chart of a preferred method of the invention is described. A length of contact material is provided (80). The contact material may either be a segment or a continuous ring of material. A length of lead wire is electrically coupled by welding to the contact material (82). The contact material is formed into a semicircular shape with locking means provided in the interior (84). Steps 80, 82 and 84 are repeated for each contact and the contacts and the wires are aligned in a mold (86). Steps 80-86 are repeated for the other half of the mold (88). The two halves of the mold are put together (90) and the body or carrier member is injection molded (92) thereby locking the locking portions of each electrode into the core of the body or carrier member.

COMPONENTS

The material comprising the body or carrier member of the array of electrodes is a flexible material, preferably elastomeric. Because electrode arrays of this type can be used as an auditory prosthesis which is inserted into the cochlea of a human ear, the flexible material is more preferably a medical grade material.

Preferred medical grade elastomers which may be utilized in the invention are silicone rubbers of the Silastic$^R$ elastomer series of medical grade elastomers, commercially available from Dow-Corning Medical Products, Midland, Mich. Silastic$^R$ MDX-4-4210 elastomer and Silastic$^R$ 382 elastomer are examples of suitable, electrically insulative, flexible, medical-grade elastomeric materials. These materials are essentially nontoxic, non-irritating, non-sensitizing and can be placed in contact with skin or other tissues without producing adverse effects. In addition, these elastomeric materials are dimensionally and thermally stable, resistant to oxidation and sunlight, and do not become hard with age.

The Silastic$^R$ 382 medical grade elastomer is supplied as two separate liquids, namely, an opaque viscous elastomeric base and a catalyst. Silastic$^R$ 382 medical grade elastomer is represented by Dow-Corning to be comprised of polydimethylsiloxane and silica filler. The catalyst is said to be a specially tested grade of stannousoctoate. When mixed together the Silastic$^R$ 382 elastomer remains workable for approximately 10 minutes and vulcanization is complete in about 30 minutes. The working and vulcanization times may be varied by changing the amount of catalyst.

Silastic$^R$ MDS-4-4210 medical grade elastomer is a clear to translucent, high strength, clean grade, silicone rubber which cures at room temperature. Silastic$^R$ MDS-4-4210 elastomer is made by mixing a curing agent with a base material in an approximate ratio of one part of curing agent to 10 parts by weight of the base material. Curing sufficient for handling of the material occurs in about 24 hours at 23 C., with full cure achieved in about three days at room temperature. Curing may be accelerated by increasing the temperature.

It is desirable that the flexible material have sufficient tensile strength to provide the desired flexibility to the finished prosthesis to allow for insertion into the cochlea. Other medical grade elastomeric materials having suitable flexibility and the other desired properties can also be used.

The contact material used in the present invention is preferably formed from platinum or platinum-iridium ribbons having a thickness typically ranging from $1.25 \times 10^{-3}$ to $5 \times 10^{-3}$ cm, and widths preferably about 0.2 mm to 0.5 mm. The contact material may either be a segment of material or it may be a continuous ring of material.

In addition to the elastomeric material and the contact material, the electrode arrays include contact wires. The contact wires are typically Teflon$^R$ flouropolymer (registered trademark of DuPont) coated platinum or platinum-iridium wires having diameters typically ranging from $1.25 \times 10^{-3}$ to $1.25 \times 10^{-2}$ cm. These wires are welded to the individual electrodes in any of a variety of positions, such as shown in FIGS. 2-4.

FABRICATIONS

The electrode arrays of the invention are fabricated, generally by forming the length of contact material into the desired shape, welding a lead or contact wire to a desired place on the contact material, arranging a desired number of contacts in each half of a mold having a generally circular cross-section which is tapered toward one end. The contacts are arranged so that the convex contact surface is in contact with the semi-circular surface of the mold. The lead wires are all aligned so that they lie generally longitudinally in the mold. Vacuum holes may be provided in the mold through which vacuum pressure may be applied to anchor the contacts in place during injection molding. Typically 1 to 10 electrodes are provided in each half of the mold. An electrode array as shown in FIG. 1 can then be formed by injection molding the body or carrier member from a flexible, electrically insulating material as is described above.

The dimensions of the array of electrodes are dictated by its intended use. The electrodes themselves should be dimensioned and positioned so as to not contact or short to a neighboring electrode. An array of electrodes used as an auditory prosthesis in a human cochlea would be dimensioned to fit into the human cochlea which has an average length (unwound) of about 32 mm. The average length of an auditory prosthesis array typically may range from 15 to 25 mm. The cross-section of the array is preferably circular or oval to fit snuggly in the cochlea. The individual electrodes may be spaced from almost touching to 15 to 25 mm apart, typically with about 1-2 mm center-to-center spacing. The auditory prosthesis is tapered with the narrow end inserted first. The narrow or tip diameter may typically range from about 0.2 mm to 0.8 mm with the wide end ranging from about 1 to 2 mm, with 1.0 to 1.4 being preferred. The width of the electrodes is preferably 0.2 mm to 0.5 mm.

The two mold halves are then fastened together so that the electrodes form pairs of preferably diametrically opposed, radially spaced electrodes. The body of the electrode array is molded from flexible material, preferably elastomeric. The body is then injection molded, preferably at room temperature.

The cure of the flexible material can be hastened by placing the mold in an oven at an elevated temperature for a desired period of time. The electrode is removed from the mold by carefully removing one half the mold at a time and trimming any excess elastomeric material away from the edges of the electrode with a sharpened device. An electrode array, for example, as shown in FIG. 1 is then provided.

What is claimed is:

1. An array of bipolar electrodes comprising:
a molded carrier member having a surface and a core, said member including at least one pair of electrodes molded therein, at least one electrode of said pair of electrodes comprising a length of contact material which is planar in a longitudinal direction of said carrier member and is formed in a semicircular shape having a convex contact surface constituting only a portion of said length of contact material and a locking portion defining an internal space, said contact material molded in said carrier member with said contact surface being the only portion of said contact material exposed at said member surface, the locking portion of said contact material being molded entirely into the core of said carrier member, said contact material connected to a lead wire molded in the core of said carrier member.

2. The array according to claim 1 wherein the convex contact surface of said contact material is flush with the surface of the carrier member.

3. The array according to claim 1 wherein a lead wire is welded to the length of contact material and molded in said carrier member and further wherein the unused end of said wire has an extent beyond said length so that it aids anchoring of the length in the carrier.

4. The array according to claim 1 wherein said length of contact material is a continuous ring.

5. The array according to claim 4 wherein said continuous ring comprises a portion of a tube of contact material.

6. The array according to claim 1 wherein said length of contact material has a first end and a second end, said first end overlapping said second end to form a closed ring.

7. The array according to claim 1 wherein said contact material froms a closed loop, said loop being embedded in said carrier except at said contact surface.

8. An array of bipolar electrodes comprising:
a molded carrier member having a surface and a core, said member including at least one pair of electrodes molded therein, said pair of electrodes each comprising a length of contact material formed in a semicircular shape having a convex contact surface and a locking portion defining an internal space, said contact material molded in said carrier member with said contact surface exposed through said member surface, said pair of electrodes being disposed so that said contact surfaces thereof are diametrically opposed to one another, the locking portion of said contact material molded into the core of said carrier member, said contact material connected to a lead wire molded in the core of said carrier member.

9. The array of claim 8 wherein each electrode of said pair of electrodes is disposed equidistantly from an end of said array.

* * * * *